(12) United States Patent
DeLaRosa et al.

(10) Patent No.: US 9,931,103 B1
(45) Date of Patent: Apr. 3, 2018

(54) COMBINATION URINARY FUNNEL AND BIOLOGICAL INDICATOR TEST DEVICE

(71) Applicants: Jacob DeLaRosa, Pocatello, ID (US); Juan Leon, Pocatello, ID (US); Andrew M. Ortgiesen, Ogden, UT (US)

(72) Inventors: Jacob DeLaRosa, Pocatello, ID (US); Juan Leon, Pocatello, ID (US); Andrew M. Ortgiesen, Ogden, UT (US)

( * ) Notice: Subject to any disclaimer, the term of this patent is extended or adjusted under 35 U.S.C. 154(b) by 291 days.

(21) Appl. No.: 14/961,438

(22) Filed: Dec. 7, 2015

Related U.S. Application Data

(60) Provisional application No. 62/090,742, filed on Dec. 11, 2014.

(51) Int. Cl.
*A61B 10/00* (2006.01)
*A61F 5/455* (2006.01)

(52) U.S. Cl.
CPC ........ *A61B 10/007* (2013.01); *A61B 10/0012* (2013.01); *A61F 5/4556* (2013.01); *A61B 2010/0006* (2013.01); *A61B 2010/0009* (2013.01)

(58) Field of Classification Search
CPC .............................. A61F 5/4556; A61B 10/007
See application file for complete search history.

(56) References Cited

U.S. PATENT DOCUMENTS

| | | | |
|---|---|---|---|
| 4,681,573 A | 7/1987 | McGovern | |
| 4,751,751 A | 6/1988 | Reno | |
| 4,756,029 A | 7/1988 | Zieve | |
| 5,605,161 A * | 2/1997 | Cross | A61B 10/007 4/144.2 |
| 5,991,932 A | 11/1999 | Wagner | |
| 6,434,757 B1 | 8/2002 | Filsouf | |
| 6,460,200 B1 | 10/2002 | Mottale | |
| 6,669,675 B2 | 12/2003 | Lipman | |
| 6,719,741 B2 | 4/2004 | Ching | |
| 8,221,367 B2 | 7/2012 | Oprandi | |
| 2007/0044213 A1 | 3/2007 | Hall | |

* cited by examiner

*Primary Examiner* — Puya Agahi
(74) *Attorney, Agent, or Firm* — QuickPatents, LLC; Kevin Prince

(57) ABSTRACT

A urinary funnel has proximal and distal openings and is preferably made from a resilient web scored to define two side panels foldable at a lower fold line that attach mutually together at a top flap. The funnel is collapsible so as to be carried in a wallet or purse. At least one biological indicator is fixed with the inner surface of the funnel structure proximate the distal opening for detecting the use of illicit drugs, pregnancy, or other biological conditions. The web may further includes a transverse slot proximate the lower fold line that is adapted to receive a biological indicator test strip therethrough. The biological indicator is applied to the biological indicator test strip that is in turn positioned through the transverse slot to rest against the inner surface of the funnel structure within the stream of urine flowing from the proximal opening to the distal opening.

20 Claims, 4 Drawing Sheets

COMBINATION URINARY FUNNEL AND BIOLOGICAL INDICATOR TEST DEVICE

CROSS-REFERENCE TO RELATED APPLICATIONS

This application claims the benefit of U.S. Provisional Patent Application 62/090,742, filed on Dec. 11, 2014, and incorporated herein by reference.

STATEMENT REGARDING FEDERALLY SPONSORED RESEARCH AND DEVELOPMENT

Not Applicable.

FIELD OF THE INVENTION

This invention relates to urinary funnels, and more particularly to a urinary funnel with a biological test indicator.

DISCUSSION OF RELATED ART

Urinary funnels for allowing women to urinate in a standing position are known in the art, and generally provide for a convenient and clean method for women to urinate without contacting toilet seats that may be unsanitary, particularly in public restrooms.

Biological indicator tests, such as drug or pregnancy tests, typically include an indicator strip that is to be placed within the urine stream to activate the biological indicator. Such devices, for both men and women, often require the strip to be held so close to the urine stream that some urine inevitably splashes onto the user's hands, which is unsanitary and may result in the user not adequately soaking the test strip with the urine.

U.S. Pat. No. 5,605,161 to Cross on Feb. 25, 1997 teaches a urinary funnel that includes a detachable urinalysis reagent strip. While such a device does provide a funnel structure for allowing a person to urinate in a standing position, the detachable urinalysis ring, once soaked in urine, is not easily handled without contacting the urine. Further, such a device, while collapsible in an axial direction with an accordion-type pleated arrangement, does not collapse down to a size suitable for carrying in a standard folded wallet.

Therefore, there is a need for a funnel device that allows both men and women to urinate in a standing position and to expose a urinalysis test or test strip to the urine stream produced thereby. Such a needed device would be collapsible to an extent readily transportable in a standard folded wallet, and would provide a means by which the test strip is detachable from the disposable funnel device and may be cleanly handled and transported. Such a needed device would be relatively inexpensive to manufacture and intuitive to use. The present invention accomplishes these objectives.

SUMMARY OF THE INVENTION

The present device is a urinary funnel comprising a collapsible funnel structure having a proximal opening and a distal opening. The funnel structure has an inner surface and an outer surface, and is made from preferably a resilient web scored to define two side panels foldable at a lower fold line that attach mutually together at a top flap. The funnel is collapsible so as to be carried in a wallet or purse.

At least one biological indicator is fixed with the inner surface of the funnel structure proximate the distal opening. A legend or indicia may be printed on the outer surface of the funnel structure to indicate how to read the results of the biological indicator after exposure to the urine. An aperture through the funnel structure may be included through which the at least one biological invocator may be viewed. A transparent material may cover the aperture to prevent fluid from spilling through the aperture.

In use, when urine flows between the proximal opening to the distal opening, the at least one biological indicator is activated by the urine to indicate a biological condition. For example, the biological indicator may be a visual indicator for detecting the use of illicit or prescription drugs by the user as evidenced by the presence of drug-related metabolites in the urine, such drugs being, for example, cannabis, alcohol, nicotine, cocaine, opiates, or the like. In one preferred embodiment the biological indicator detects the presence of pregnancy-indicating hormones in the urine.

In one embodiment, the web further includes a transverse slot proximate the lower fold line that is adapted to receive a biological indicator test strip therethrough. The biological indicator is applied to the biological indicator test strip that is in turn positioned through the transverse slot to rest against the inner surface of the funnel structure within the stream of urine flowing from the proximal opening to the distal opening. In such an embodiment, a liquid-absorbing material covers the transverse slot and a portion of the inner surface of the web, thereby defining a test strip pocket adapted to receive the biological indicator test strip therein.

In one embodiment the biological indicator test strip is partially enclosed in a test strip cartridge with an exposed portion of the test strip projecting away therefrom and adapted to be inserted into the transverse slot. In such an embodiment the outside surface of the funnel structure further includes a test strip cartridge attachment mechanism for selectively and temporarily securing the test strip cartridge to the funnel structure. A cartridge cap may be included and adapted for covering the exposed portion of the test strip when the test strip cartridge is removed from the funnel structure.

The present invention is a funnel device that allows both men and women to urinate in a standing position and to expose a urinalysis test or test strip to the urine stream produced thereby. The present device is collapsible so as to be readily carried in a standard folded wallet, and provides a means by which the test strip is detachable from the disposable funnel device and may be cleanly handled and transported. The present invention is relatively inexpensive to manufacture and intuitive to use. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
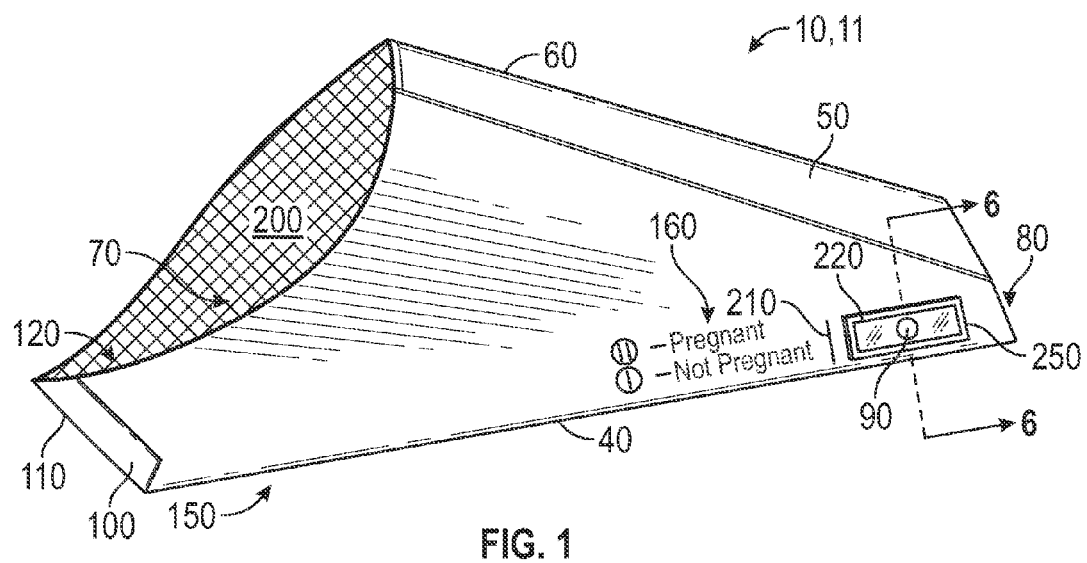
FIG. 1 is a perspective view of the invention, showing a resilient web of the invention folded and secured in a deployed configuration.

FIG. 1 shows a urinary funnel 10 comprising a collapsible funnel structure 11 having a proximal opening 70 and a distal opening 80. The funnel structure 11 has an inner surface 21 and an outer surface 29, a hydrophobic coating 200 preferably being applied to at least the inside surface 21 thereof. The funnel structure 11 may be a folded web 20, a telescoping plastic apparatus (not shown), a resilient closed-foam material (not shown), or the like.

Preferably the funnel structure 11 comprises a resilient web 20 (FIG. 2) scored to define two side panels 30 foldable at a lower fold line 40, and a top flap 50 defined by a top fold line 60 at one of the side panels 30 and fixable to the other side panel 30 to define the proximal opening 70 and the distal opening 80. The resilient web 20 may be paper, plastic, or the like, and may be stamped or die-cut from a larger sheet of the resilient web material.

In one embodiment the resilient web 20 further includes a proximal flap 100 (FIG. 1) defined by a proximal fold line 110 at one of the side panels 30 that is fixable to the other side panel 30 to define a proximal trough 120 at the proximal opening 70 which is adapted to catch urine 15 from a standing urinating person, either male or female. The top flap 50 and the proximal flap 100 may be adhered to the other side panel 30 with adhesive 190, ultrasonic bonding, or other suitable means.

Figure 5:
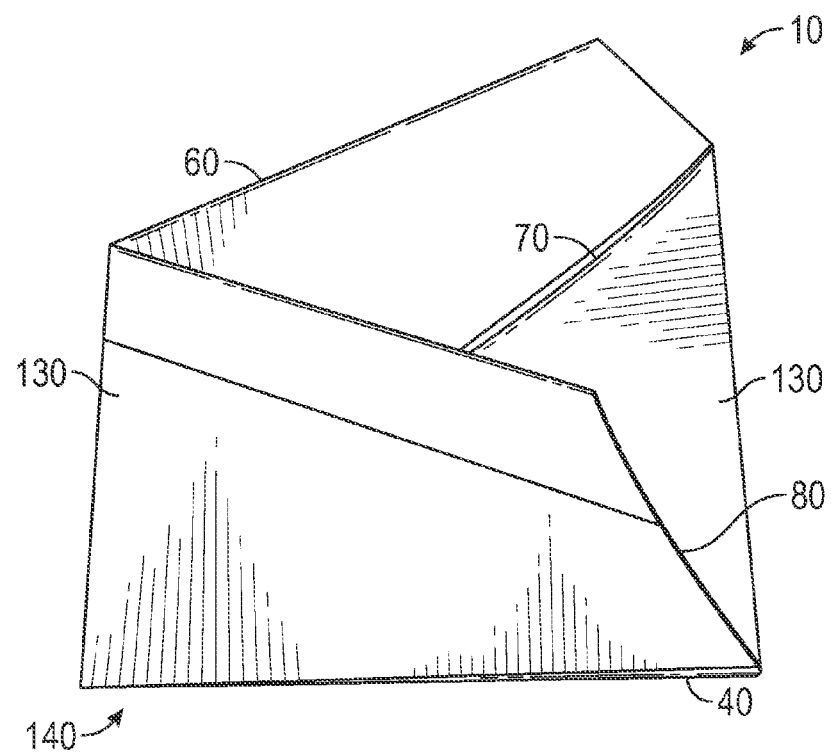
FIG. 5 is a side elevational view of the invention as folded into a collapsed configuration.

Preferably the resilient web 20 further includes a pair of score lines 130 (FIGS. 3 and 5) each generally orthogonal to the lower fold line 40, such that the funnel 10 may be folded into a flattened, collapsed configuration 140 no larger than a dollar bill folded in half vertically and stored in a standard wallet, for example.

At least one biological indicator 90 is fixed with the inner surface 21 of the funnel structure 11 proximate the distal opening 80. The hydrophobic coating 200 is not included in the area of the biological indicator so that the urine 15 may fully contact the at least one biological indicator 90. In one embodiment the at least one biological indicator 90 is positioned on the funnel structure 11 so as to be visible through the distal opening 80 (FIG. 4). A legend or indicia 160 (FIGS. 1 and 3) may be printed on the outer surface 29 of the funnel structure 11 to indicate how to read the results of the biological indicator 90 after exposure to the urine 15. An aperture 250 through the funnel structure 11 may be included through which the at least one biological invocator 90 may be viewed. A transparent material 260 may cover the aperture 250 to prevent fluid from spilling through the aperture 250.

In use, when urine 15 flows between the proximal opening 70 to the distal opening 80, the at least one biological indicator 90 is activated by the urine 15 to indicate a biological condition. For example, the biological indicator 90 may be a visual indicator for detecting the use of illicit or prescription drugs by the user as evidenced by the presence of drug-related metabolites in the urine 15, such drugs being, for example, cannabis, alcohol, nicotine, cocaine, opiates, or the like. In one preferred embodiment the biological indicator 90 detects the presence of pregnancy-indicating hormones in the urine 15.

Figure 2:
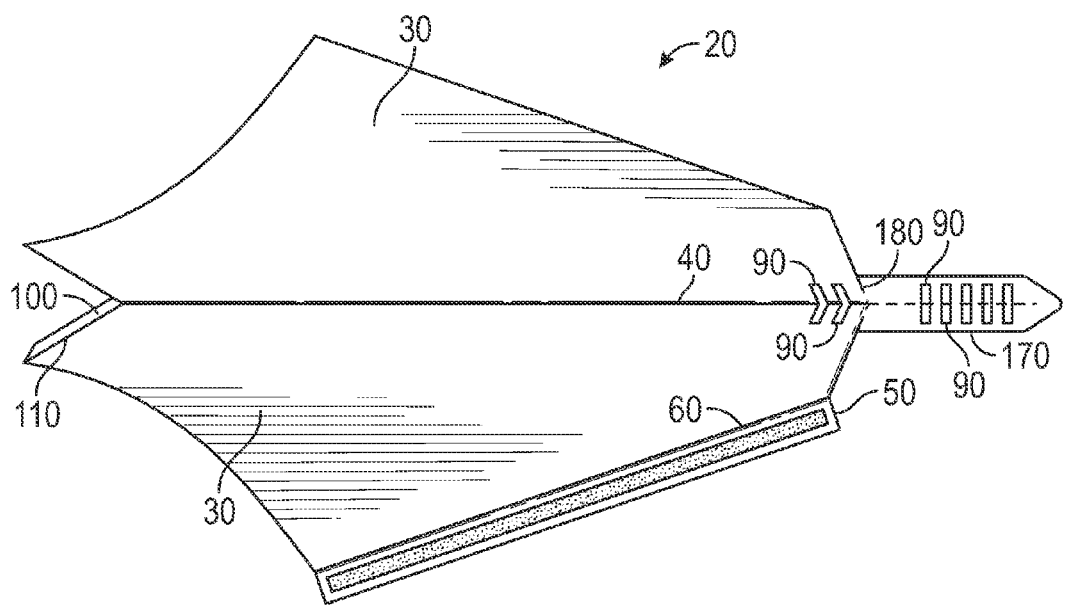
FIG. 2 is a top plan view of the invention in a flat configuration.
Figure 3:
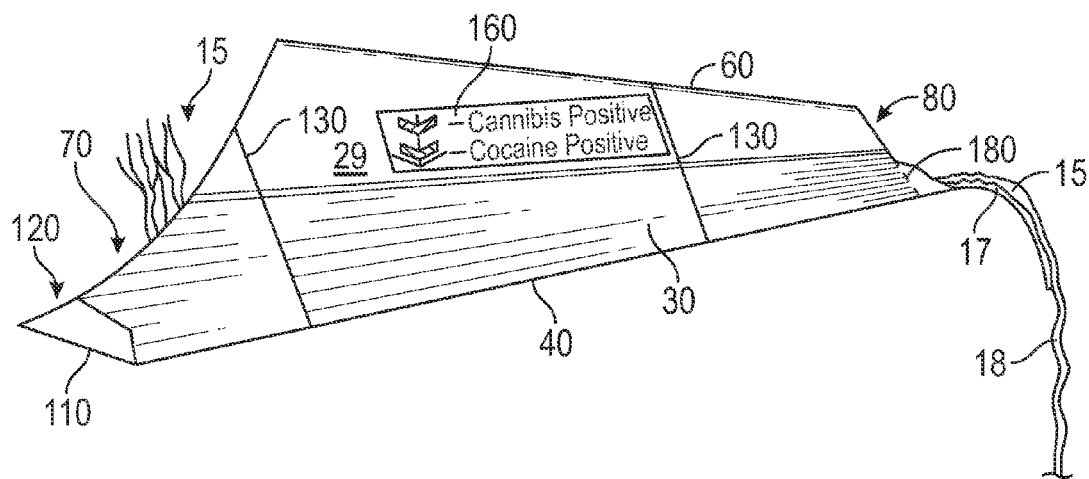
FIG. 3 is a left-side elevational view of the invention.
Figure 4:
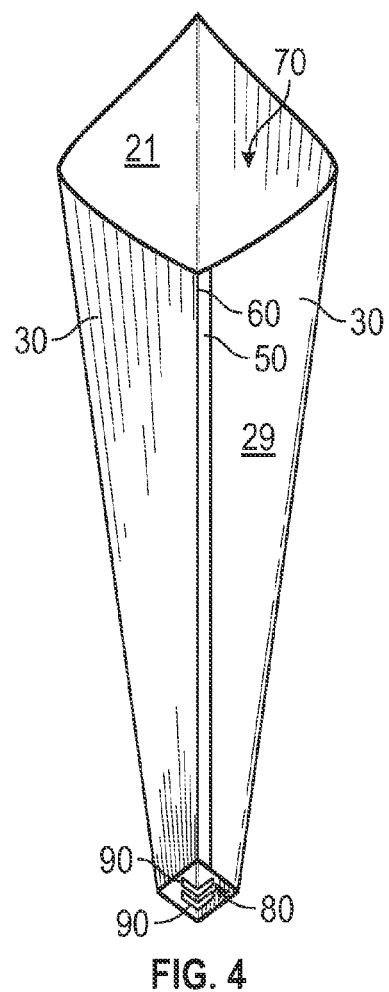
FIG. 4 is a top plan view of the invention.

In one embodiment the resilient web 20 further includes a test strip 170 extending past the distal opening 80 (FIGS. 2 and 3). Such a test strip 170 is detachable from the distal opening 80 at a perforation 180 proximate the distal opening 80, and further includes the at least one biological indicator 90 thereon. Such a test strip 170 may be shaped to direct urine 15 flowing through the distal opening 80 downwardly in a coherent stream 18 (FIG. 3).

In one embodiment, the web 20 further includes a transverse slot 210 proximate the lower fold line 40 that is adapted to receive a biological indicator test strip 220 therethrough. The biological indicator 90 is applied to the biological indicator test strip 220 that is in turn positioned through the transverse slot 210 to rest against the inner surface 21 of the funnel structure 11 within the stream of urine 15 flowing from the proximal opening 70 to the distal opening 80. As such, a non-exposed portion of the test strip 220 may be pulled to remove the test strip 220 from the funnel structure 11 after urinating, with the funnel structure 11 thereafter being disposed of.

Figure 6:
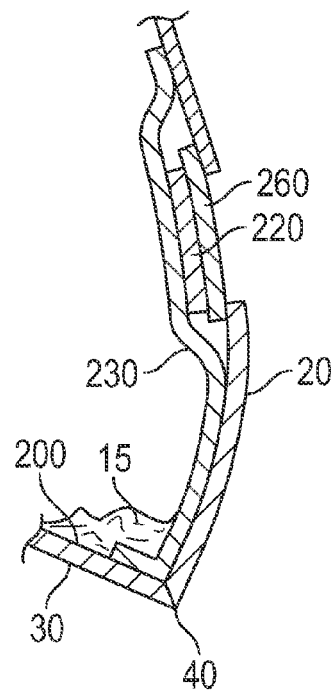
FIG. 6 is a cross-sectional view of the invention, taken along lines 6-6 of FIG. 1.

In such an embodiment, a liquid-absorbing material 230 (FIG. 6), such as an open-cell foam or a sponge material, covers the transverse slot 210 and a portion of the inner surface 21 of the web 20, thereby defining a test strip pocket 240 adapted to receive the biological indicator test strip 220 therein. Such a liquid-absorbing material 230 may extend down to the fold line 40 or the lower portion of the funnel structure 11 to ensure collection of urine 15 thereby and the transportation of the urine 15 through capillary action up to the test strip 220.

Figure 7:
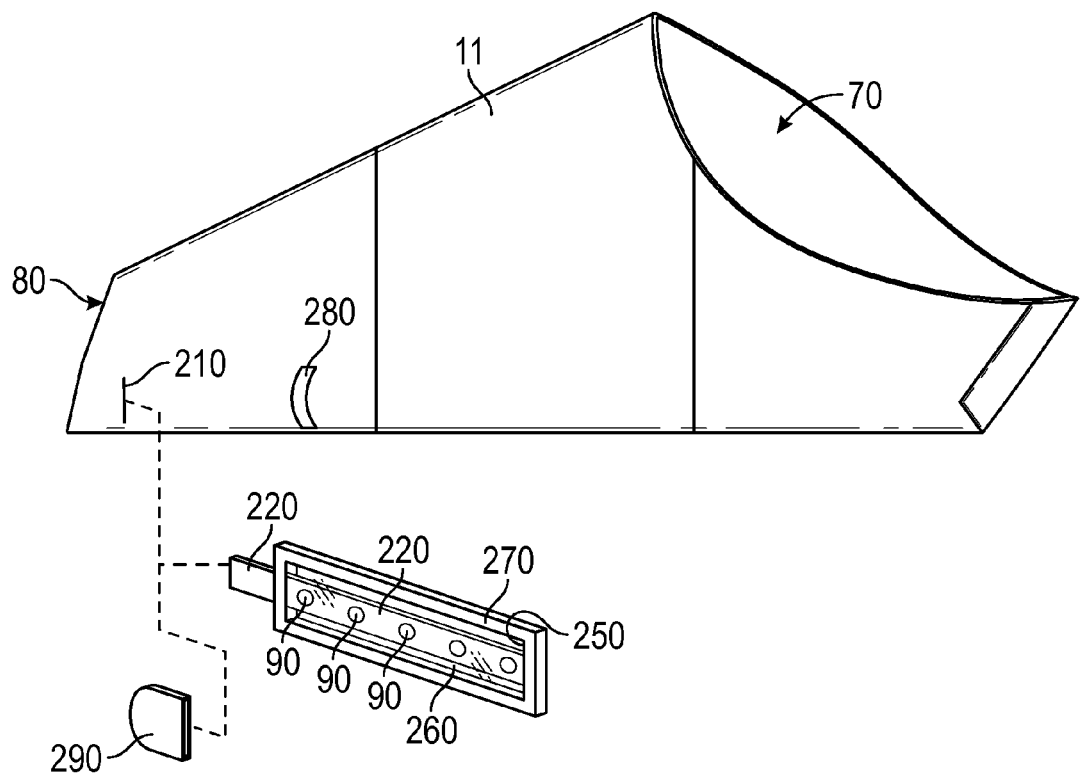
FIG. 7 is an exploded side elevational view of an alternate embodiment of the invention.

In one embodiment the biological indicator test strip 220 is partially enclosed in a test strip cartridge 270 (FIG. 7) with an exposed portion of the test strip 220 projecting away therefrom and adapted to be inserted into the transverse slot 210. In such an embodiment the outside surface 29 of the funnel structure 11 further includes a test strip cartridge attachment mechanism 280 for selectively and temporarily securing the test strip cartridge 270 to the funnel structure 11. A cartridge cap 290 may be included and adapted for covering the exposed portion of the test strip 220 when the test strip cartridge 270 is removed from the funnel structure 11. As such, after urination the cap 290 may be affixed to the test strip cartridge 270 to prevent the urine-soaked test strip 220 from contaminating surrounding surfaces.

While a particular form of the invention has been illustrated and described, it will be apparent that various modifications can be made without departing from the spirit and scope of the invention. For example, one urinary funnel 10 may be produced for indicating illicit drug use, while another may be produced for determining pregnancy status, blood sugar levels, or the like. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:
1. A urinary funnel comprising:
   a collapsible funnel structure having a proximal opening and a distal opening, the collapsible funnel structure having an inner surface and an outer surface;
   at least one biological indicator fixed with the inner surface proximate the distal opening and a lower side of the urinary funnel;
   whereby when urine flows between the proximal opening to the distal opening, the at least one biological indicator is activated by the urine to indicate a biological condition;
   further including a transverse slot proximate the lower side of the urinary funnel and adapted to receive a biological indicator test strip therethrough, whereby urine when flowing from the proximal opening to the distal opening contacts at least a portion of the biological indicator test strip inserted through the transverse slot; and
   wherein the biological indicator test strip is partially enclosed in a test strip cartridge with an exposed portion of the biological indicator test strip projecting away therefrom and adapted to be inserted into the transverse slot, the outside surface of the collapsible funnel structure further including a test strip cartridge attachment mechanism for selectively and temporarily securing the test strip cartridge to the collapsible funnel structure.

2. The urinary funnel of claim 1 wherein the collapsible funnel structure comprises a resilient web scored to define two side panels foldable at a lower fold line, and a top flap defined by a top fold line at one of the side panels and fixable to the other side panel to define the proximal opening and the distal opening.

3. The urinary funnel of claim 2 wherein the resilient web further includes a proximal flap defined by a proximal fold line at one of the side panels and fixable to the other side panel to define a proximal trough at the proximal opening adapted for catching urine from a standing urinating person.

4. The urinary funnel of claim 2 wherein the resilient web further includes a pair of score lines each generally orthogonal to the lower fold line, whereby the urinary funnel may be folded into a flattened, collapsed configuration.

5. The urinary funnel of claim 4 when in the collapsed configuration is no larger in width or height than a dollar bill folded vertically down the center, whereby the urinary funnel may be transported in a standard wallet.

6. The urinary funnel of claim 1 wherein the at least one biological indicator is positionable on the collapsible funnel structure so as to be visible through the distal opening.

7. The urinary funnel of claim 1 wherein an indicia is printed on the outer surface of the collapsible funnel structure, the indicia indicating how to read the results of the biological indicator after exposure to the urine.

8. The urinary funnel of claim 1 wherein the biological indicator is a visual indicator for detecting a presence of cannabis metabolites in the urine.

9. The urinary funnel of claim 1 wherein the biological indicator is a visual indicator for detecting a presence of cocaine metabolites in the urine.

10. The urinary funnel of claim 1 wherein the biological indicator is a visual indicator for detecting a presence of pregnancy-indicating hormones in the urine.

11. The urinary funnel of claim 1 wherein the biological indicator is a visual indicator for detecting a presence of alcohol metabolites in the urine.

12. The urinary funnel of claim 1 wherein the biological indicator is a visual indicator for detecting a presence of nicotine metabolites in the urine.

13. The urinary funnel of claim 2 wherein the resilient web further includes a test strip extending past the distal opening, the test strip detachable from the distal opening at a perforation proximate the distal opening, the test strip including the at least one biological indicator thereon.

14. The urinary funnel of claim 13 wherein the test strip is shaped to direct urine flowing through the distal opening downwardly in a coherent stream.

15. The urinary funnel of claim 1 wherein the biological indicator is a visual indicator for detecting a presence of opioids in the urine.

16. The urinary funnel of claim 1 wherein the collapsible funnel structure is made from a hydrophobic material or includes a hydrophobic coating on at least the inner surface thereof, except in the area of the at least one biological indicator.

17. The urinary funnel of claim 1 further including a liquid-absorbing material covering the transverse slot and a portion of the inner surface of the collapsible funnel structure, defining a test strip pocket adapted to receive a biological indicator test strip therein.

18. The urinary funnel of claim 1 wherein the collapsible funnel structure includes at least one aperture therethrough through which at least one biological indicator may be viewed.

19. The urinary funnel of claim 18 wherein the at least one aperture is covered with a transparent material.

20. The urinary funnel of claim 1 further including a cartridge cap adapted for covering the exposed portion of the biological indicator test strip when the test strip cartridge is removed from the collapsible funnel structure.

* * * * *